United States Patent
Zourob (10) Patent No.: US 10,151,749 B2
(45) Date of Patent: Dec. 11, 2018

(54) METHOD AND KIT FOR THE DETECTION OF MICROORGANISMS

(71) Applicant: Alfaisal University, Riyadh (SA)

(72) Inventor: Mohammed Zourob, Riyadh (SA)

(73) Assignee: Alfaisal University, Riyadh (SA)

(*) Notice: Subject to any disclaimer, the term of this patent is extended or adjusted under 35 U.S.C. 154(b) by 300 days.

(21) Appl. No.: 14/852,526

(22) Filed: Sep. 12, 2015

(65) Prior Publication Data
US 2017/0038370 A1    Feb. 9, 2017

Related U.S. Application Data

(63) Continuation-in-part of application No. 14/819,195, filed on Aug. 5, 2015.

(51) Int. Cl.
*G01N 33/543* (2006.01)
*G01N 33/544* (2006.01)
*G01N 33/569* (2006.01)

(52) U.S. Cl.
CPC ..... *G01N 33/54306* (2013.01); *G01N 33/544* (2013.01); *G01N 33/54326* (2013.01); *G01N 33/56911* (2013.01); *G01N 33/56916* (2013.01); *G01N 33/56922* (2013.01); *G01N 33/56938* (2013.01)

(58) Field of Classification Search
None
See application file for complete search history.

(56) References Cited

U.S. PATENT DOCUMENTS

| | | | | |
|---|---|---|---|---|
| 4,013,514 A | * | 3/1977 | Wildi | C12H 1/003 426/12 |
| 4,775,636 A | * | 10/1988 | Moeremans | G01N 33/532 436/518 |
| 4,859,612 A | * | 8/1989 | Cole | G01N 33/54313 436/523 |
| 5,451,504 A | * | 9/1995 | Fitzpatrick | G01N 33/558 435/7.2 |
| 5,801,063 A | * | 9/1998 | Grandics | G01N 33/86 422/402 |
| 2003/0049864 A1 | * | 3/2003 | Nakamura | G01N 33/5304 436/518 |
| 2011/0160636 A1 | * | 6/2011 | Bansal | C07K 16/18 604/6.09 |
| 2011/0262989 A1 | * | 10/2011 | Clarizia | C07K 1/22 435/173.9 |
| 2016/0370356 A1 | * | 12/2016 | Badu-Tawiah | G01N 33/54353 |

OTHER PUBLICATIONS

Bagherbaigi et al. "Cotton fabric as an immobilization matrix for low-cost and quick colorimetric enzyme-linked immunosorbent assay (ELISA)" Anal. Methods, 2014, 6, 7175-7180 (Year: 2014).*

(Continued)

*Primary Examiner* — Christine Foster
(74) *Attorney, Agent, or Firm* — Geeta Kadambi; Riddhi IP LLC (57) ABSTRACT

There is provided a method of detecting an analyte in a sample. The method is based on colorimetry and also on the binding affinity between the analyte and a chemical substrate which may be a recognition receptor thereof. The method involves a support and a colored carrier. A kit for use in the detection is also provided.

13 Claims, 5 Drawing Sheets

(56) References Cited

OTHER PUBLICATIONS

Oxford Dictionaries, definition of "swab", retrieved from https://en.oxforddictionaries.com/definition/swab on Feb. 24, 2018, two pages.*

Sadir et al. "Fiber based enzyme-linked immunosorbent assay for C-reactive protein" Sensors and Actuators B: Chemical, vol. 205, Dec. 15, 2014, pp. 50-60, http://dx.doi.org/10.1016/j.snb.2014.08.051.*

* cited by examiner

METHOD AND KIT FOR THE DETECTION OF MICROORGANISMS

CROSS REFERENCE TO RELATED APPLICATION

This application claims priority to pending patent application Ser. No. 14/819,195 filed on 5 Aug. 2015 and is a continuation-in-part of the said application. The pending U.S. application Ser. No. 14/819,195 is hereby incorporated by reference in its entireties for all of its teachings.

FIELD OF TECHNOLOGY

This disclosure relates generally to the detection of microorganisms. More specifically, this disclosure relates to a method and associated kit for the detection of an analyte in a sample. The sample may be a patient sample or a sample from a food source, a food processing plant, a human, an animal, a hospital environment or any other environment.

BACKGROUND

Foodborne diseases (FBD) are the infectious and toxic diseases caused by agents that enter the body through the ingestion of food (velusamy et al., 2010). These agents commonly referred to as pathogens include bacteria, viruses, parasites, toxins and metals. These agents can also be transmitted through the food chain reaching humans. For example, Salmonella spp. is a bacterial zoonotic pathogen, and is ubiquitous in the environment. They are commonly found in the gut and intestinal tract of animals including farmed, domestic and wild animals. There are numerous routes through the food chain (Herman et al., 2008). Salmonella is one of the most common pathogen causing human bacterial gastroenteritis. This has been outlined in various reports (EFSA, 2010). It is known that in the European Union countries there has been a total of 131,468 confirmed cases of human salmonellosis in the year 2008 (Zweifel et al., 2012). Poultry and eggs are considered to be the most important carriers for these foodborne diseases especially for Salmonella and Campylobacter which can be transmitted to humans. In Saudi Arabia, food of poultry origin causes 29.3% of poisoning cases (Haider and EL-Eied, 2005). Salmonellosis is a public health concern. An estimated 93.8 million cases of gastroenteritis are developed in places such as tropical countries, Europe, United-States, South America, Asia (Rane, 2011; Borges et al., 2013; Henry et al., 2013). Generally human salmonellosis cases are associated with consumption of contaminated egg, poultry products (Zaki et al., 2009). It has been reported that about 90-95% of non-typhoid salmonellosis increases by consumption of contaminated food-stuffs (poultry and other meat products) (Andreoletti et al., 2008). Previous studies showed that salmonellae are present in poultry processing wastes in a surprisingly constant relation with fecal coliforms (in excess of 1 Salmonella per 500 fecal coliforms) (Hoadley et al., 1974). Salmonella Enteritidis and Salmonella Typhimurium are typical serovars belonging to the S. enterica subspecies (79.9% of all known serovars in human cases), significant causes of foodborne illness in humans with 95,548 reported cases in the European Union in 2011 (Zweifel and Stephan, 2012; Ahmed et al., 2014). However, it has been reported that S. Enteritidis is reported more frequently than S. Typhimurium in many European countries. Both of these bacteria are currently the most widely spread critical pathogens causing foodborne illnesses in humans and animals (Park et al., 2014).

Staphylococcus aureus is also considered one of the most common sources of food poisoning resulting from consumption of contaminated food (EI-Jakee et al., 2013), raw meat, meat product, dairy products and ready-to-eat foods. For example, it is one of the top five pathogens that contribute to the most foodborne illnesses in America. About 76 million cases of illnesses and 5000 deaths are reported each year according to the Centre for Disease Control and Prevention (2012) (World Health Organization, 2007; Sung et al., 2013). Staphylococcus aureus enterotoxins (SEs) which contains some proteins that have a thermo-stability extracellularly are caused by S. aureus. Staphylococcal food poisoning (SFP) caused by the ingestion of food contaminated with SEs is the second most commonly reported foodborne illness (Argudin et al., 2010). After food poisoning by Staphylococcus aureus, symptoms usually appear within a few hours of eating the contaminated food. The most common symptoms are nausea, vomiting, abdominal cramping, and prostration. Food that is most frequently infected by Staphylococcus aureus includes meat and meat products, poultry and egg products (Stehulak, 2011).

Different methods depending on various scientific principles are used for the detection of pathogenic bacteria relating foodborne diseases. Conventional methods include culture-depending methods, microscopic, PCR, serological and biochemical methods. These methods are still used but they generally present some disadvantages. For example, they are time-consuming, expensive and have and a limited sensitivity. Immunoassay is one of the detection methods which depends on the antigen-antibody reaction resulting in a production of a signal which can be measured (fingerova et al., 2011). This technique is widely used for detection of pathogens (Webster et al., 2004) and food toxins like mycotoxins (Casale et al., 1988). Many types of immunoassay techniques are available such as ELIZA, immunomagnetic, immunofluorescence and radioimmunoassay. Among these techniques microtitre plate-based and lateral flow methods are the most commonly used in agricultural biotechnology (Shan, 2011). Immunoassay methods provide some advantages over conventional methods. For example, high specificity, sensitivity and portability. Accordingly, most immunoassay tests can be achieved utilizing kits or small apparatuses (Lesnik, 2000). This facilitates onsite and point-of-care analysis. Optical immunoassay including fluorescence, chemiluminscence, electrochemiluminscence, surface Plasmon resonance which combine antigen-antibody reaction with optical measurements are one of the most common immunoassay techniques. This is because it uses visible light radiation. Also, a rapid signal production is obtained which decreases the time needed to complete the bioassay test. Use of nanoparticles such as magnetic beads and fluorescent beads can improve sensitivity and performance of optical immunosensors (Tang et al., 2013), magnetic-bead based enzyme immunoassay with fluorescence has been used for detection of Bacillus globigii spores and B. globigii (Farrell et al., 2005).

Recent trends in food technology and the increasing interest in food safety and quality have led microbiologists to explore and develop new and rapid detection methods which can give precise results in the shortest time (Dostalek et al., 2005).

There is still a need for more simple, efficient and low-cost methods for detecting microorganisms.

SUMMARY

This disclosure is drawn to a method of detecting an analyte in a sample. The method is based on colorimetry and also on the binding affinity between the analyte and a chemical substrate which may be a recognition receptor thereof. The method involves the use of a support and a colored carrier which consists for example of nano-spheres or magnetic beads. The support may be a cotton swab or any support having a surface that is dielectric, a polymer, a piece of cloth, a paper, or a metal. The sample may be from various origins including a food source such as a meat source, a human, an animal, an environment such as a food processing plant, a grocery store, a hospital, a school, an industrial plant. The analyte includes for example *Salmonella typhimurium, Salmonella enteritidis, Staphylococcus aureus, Campylobacter jejuni, Listeria monocytogenes, Escherichia coli* or any other bacterium. This disclosure is also drawn to a kit associated to the method.

Several embodiments for the detection method and associated kit of this disclosure are outlined below.

In an embodiment, this disclosure provides for a method of detecting an analyte in a sample, comprising: (a) providing a support of a first color; (b) attaching on a surface of the support, a chemical substrate having a binding affinity with the analyte to be detected, to obtain a functionalized support; (c) contacting the functionalized support with the sample; (d) providing a carrier of a second color different from the first color and capable of masking the first color; (e) attaching on a surface of the carrier, the chemical substrate having a binding affinity with the analyte, to obtain a functionalized carrier; (f) contacting the functionalized support obtained at step (c) with the functionalized carrier, such that a visual inspection of the support reveals only the second color; and (g) submitting the support obtained at step (f) to a step aimed at removing the carrier from the support, wherein persistence of the second color is indicative of the presence of the analyte in the sample, and disappearance of the second color is indicative of the absence of the analyte.

In one embodiment, the method further comprises a step of (a1) activating the support prior to step (b) to obtain an activated support having a chemical group on a surface thereof.

In one embodiment, step (c) comprises swabbing a surface with the functionalized support.

In one embodiment, step (f) comprises soaking the functionalized support obtained at step (c) in an aqueous solution containing the functionalized carrier.

In one embodiment, step (g) comprises a washing step which is performed with a buffer solution including a phosphate buffer solution.

In one embodiment, the carrier consists of magnetic beads and step (g) comprises passing the support over a magnet.

In one embodiment, the analyte is a bacterium selected from the group consisting of *Salmonella typhimurium, Salmonella enteritidis, Staphylococcus aureus, Campylobacter jejuni, Listeria monocytogenes* and *Escherichia coli*.

In one embodiment, the chemical substrate is of biological origin.

In one embodiment, the chemical substrate is a specific recognition receptor having a binding affinity with a specific pathogen, or the chemical substrate is a general recognition receptor having a binding affinity with a group of pathogens.

In one embodiment, the chemical substrate is selected from the group consisting of an antibody, a fragment of an antibody, a peptide, an aptamer, a protein, an engineered protein, a polymeric receptor and a chemical receptor.

In one embodiment, the support is a cotton swab, an object having a surface that is dielectric, a polymer, a piece of cloth, a paper or a metal.

In one embodiment, the carrier consists of nano-spheres capable of attaching the chemical substrate on their surface.

In one embodiment, the first color is a light color including color white.

In one embodiment, the second color is selected from the group consisting of black, green, blue, yellow, red, purple and a combination thereof.

In one embodiment, the carrier consists of colored beads of the same color or of different colors.

In one embodiment, the functionalized carrier consists of colored beads of different colors, each set of beads of the same color being attached to a different chemical substrate.

In one embodiment, the sample is from a patient or from a food source including a meat source, a food processing plant including a meat processing plant, a human, an animal, the environment including a hospital, a grocery store, and a school.

In another embodiment, this disclosure provided for a method of detecting an analyte in a sample, comprising: (a) providing a cotton swab; (a1) activating the cotton swab to obtain an activated cotton swab with cellulose molecules having aldehyde (CHO) groups; (b) attaching on the activated cotton swab, a chemical substrate having a binding affinity with the analyte, to obtain a functionalized cotton swab; (c) swabbing a surface with the functionalized cotton swab; (d) providing colored nano-spheres; (e) attaching on the nano-spheres, the chemical substrate having a binding affinity with the analyte, to obtain functionalized nano-spheres; (f) contacting the functionalized cotton swab obtained at step (c) with the functionalized nano-spheres, such that a visual inspection of the cotton swab reveals only the color of the nano-spheres; and (g) submitting the cotton swab obtained at step (f) to a step aimed at removing the carrier from the cotton swab, wherein persistence of the color of the nano-spheres is indicative of the presence of the analyte in the sample, and disappearance of the color is indicative of the absence of the analyte.

In yet another embodiment, this disclosure provided for a kit for use in the detection of an analyte in a sample, comprising: (i) a support of a first color and having attached on a surface thereof a chemical substrate having a binding affinity with the analyte to be detected; (ii) an aqueous solution containing a carrier of a second color different from the first color and capable of masking the first color, the carrier having attached on a surface thereof the chemical substrate having a binding affinity with the analyte to be detected; and (iii) a buffer solution and/or a magnet.

Other features will be apparent from the accompanying drawings and from the detailed description that follows.

BRIEF DESCRIPTION OF DRAWINGS

Example embodiments are illustrated by way of example only and not limitation, with reference to the figures of the accompanying drawings, in which like references indicate similar elements and in which.

Other features of the present disclosure will be apparent from the accompanying drawings and from the detailed description of embodiments that follows.

DETAILED DESCRIPTION

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a" or "an" when used in conjunction with the term "comprising" in the claims and/or the description may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

This disclosure is drawn to a method of detecting an analyte in a sample. The method is based on colorimetry and also on the binding affinity between the analyte and a chemical substrate which may be a recognition receptor thereof. The method involves the use of a support and a colored carrier which consists for example of nano-spheres or magnetic beads. The support may be a cotton swab or any support having a surface that is dielectric, a polymer, a piece of cloth, a paper, or a metal. The sample may be from various origins including a food source such as a meat source, a human, an animal, an environment such as a food processing plant, a grocery store, a hospital, a school, an industrial plant. The analyte includes for example *Salmonella typhimurium, Salmonella enteritidis, Staphylococcus aureus, Campylobacter jejuni, Listeria monocytogenes, Escherichia coli* or any other bacterium. This disclosure is also drawn to a kit associated to the method.

Figure 1:
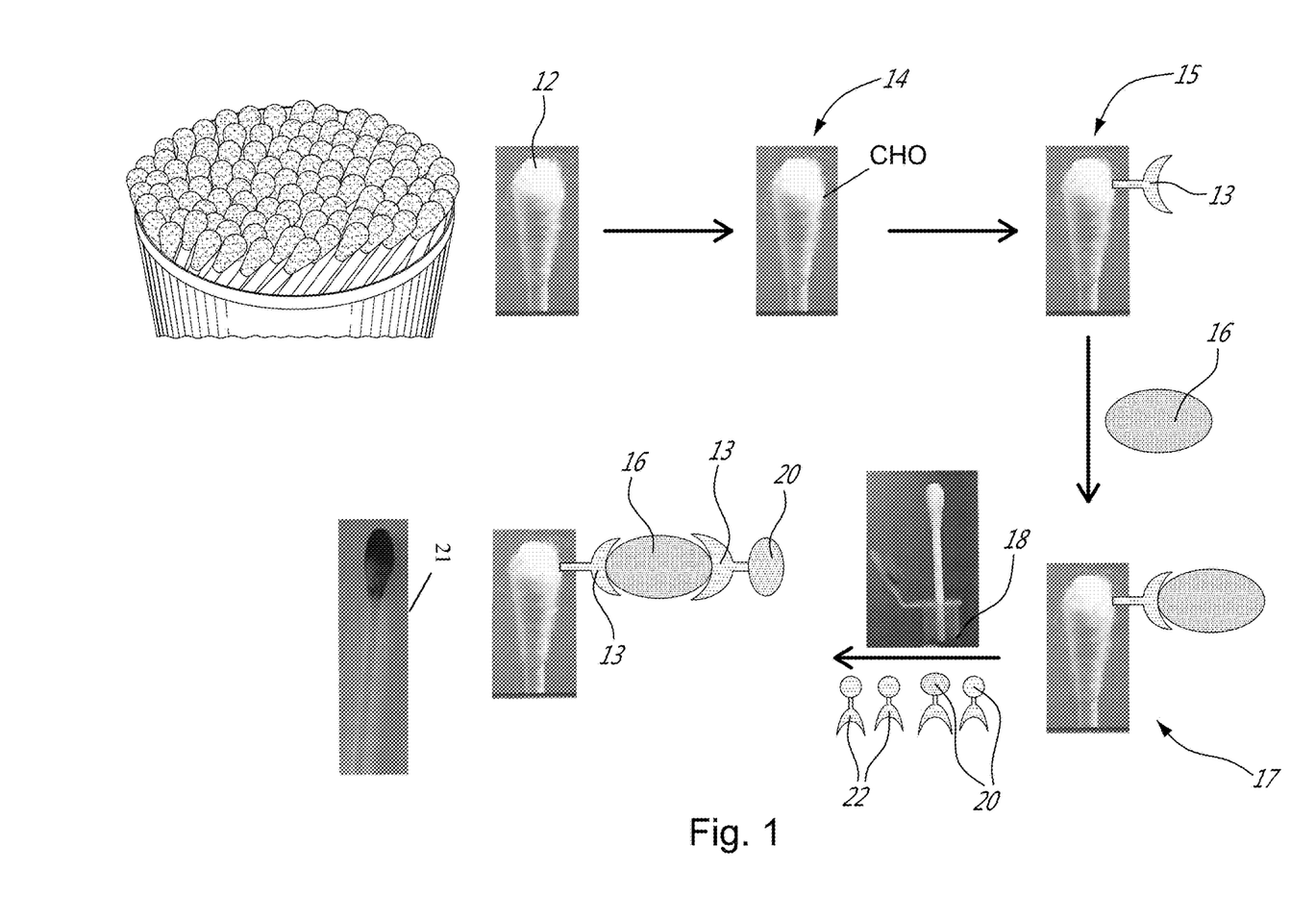
FIG. 1 outlines the steps of the detection method of this disclosure.

The detection method of this disclosure is outlined in FIG. 1. In a first step, a support which may be a cotton swab 12 as illustrated in the figure is activated to obtain an activated cotton swab 14. The cotton swab is made up of cotton wrapped round the tip of a stick in shape of a cone. The tip of a swab made up of a cone shape cotton is activated. This activation step consists of treating the cotton swab 12 as will be described in detail below, such as to provide aldehyde groups on the cellulose molecules of the cotton, to obtain the activated cotton swab 14. As will be understood by a skilled person, the chemical group on the surface of the support may be any chemical group that may be used to attach a chemical substrate 13 on the surface of the support. Accordingly, the nature of the chemical group will depend on the support and also on the chemical substrate. The chemical substrate 13 may be a recognition receptor of the analyte to be detected. Also, the chemical substrate 13 may be specific to a given analyte, i.e., binds specifically to that analyte, or the chemical substrate 13 may be general to a group of analytes, i.e., binds to any analyte member of the group. As will be understood by a skilled person, the chemical substrate may be of biological origin.

The activated cotton swab 14 is then functionalized by attaching the chemical substrate or recognition receptor 13 and 22 on its surface, thereby obtaining a functionalized support 15. The functionalized support 15 is then put into contact with the sample to be analyzed that may or may not contain the analyte 16. When the analyte 16 is present in the sample, it binds to the functionalized support 15 through the chemical substrate or recognition receptor 13 and 22.

The functionalized cotton swab having thereon the analyte 17 is soaked into a solution 18 comprising a functionalized colored carrier, which consists of a colored carrier 20 having attached on a surface thereof a chemical substrate or recognition receptor 13. As can be seen in FIG. 1, the colored carrier 20 is in the form of nano-spheres.

Upon coming into contact with the functionalized nano-spheres solution 18, the cotton swab takes the color of the nano-spheres. Indeed, the color of the nano-spheres is a color capable of masking the color of the support. In the embodiment illustrated in the figure, the support (cotton swab) is white and the color of the nano-spheres 21 which may be any other color masks the color white. In the functionalized nano-spheres solution 18, the nano-spheres may be all of the same color, or they may be of various different colors. In embodiments when the nano-spheres are of various different colors, a different chemical substrate may be attached a set of color and the method may allow for the detection of more than one analyte in the sample.

In the method of this disclosure, the cotton swab is further submitted to a washing step as will be described in detail below. If the analyte is present in the sample, it will bind to the chemical substrate or recognition receptor on the nano-spheres and the washing step will not disrupt the binding. The color of the nano-spheres will thus persist after the washing. Accordingly, persistence of the color of the nano-spheres is indicative of the presence of the analyte in the sample.

On the other hand, if the analyte is absent from the sample, no binding will occur, and the washing will remove the colored nano-spheres leading to the disappearance of the color. In other words, washing will reveal the color white. Accordingly, disappearance of the color is indicative of the absence of the analyte from the sample.

As will be understood by a skilled person, the washing step is aimed at removing non-bonded nano-spheres from the support. This step may comprise passing the support over a magnet. In these embodiments, the nano-spheres may be magnetic beads.

Materials and Methods

Bacterial strains and culture conditions: *Salmonella typhimurium* (ATCC14028) was obtained from Dr. Ronald J. W.

Lambert, Cranfield University while *Salmonella enteritidis* (ATCC13076), *Staphylococcus aureus* (ATCC6538), *Listeria monocytogenes* (ATCC7644), *Escherichia coli* (ATCC8739) and *Campylobacter jejuni* (ATCC 29428) were purchased from American Type Culture Collection (Manassas, Va.). Stock cultures of all strains except *C. jejuni* were maintained at −80° C. in 20% glycerol solution. Prior to use, the frozen culture was activated in trypticase soy broth (TSB, Oxoid, Hampshire, UK) at 37° C. with two consecutive transfers after an 18±20 h incubation period. Following incubation, the culture was centrifuged at 10,000×g for 10 min at 4° C. and washed twice in trypticase soy broth. Cell suspensions were prepared by adjusting the OD600 to 0.5, which is equivalent to $10^8$ CFU/ml. then serially diluted from 1 to $10^{-8}$ with trypticase soy broth.

Preparation of *Campylobacter jejuni* culture: Stock cultures of *C. jejuni* were grown for 4 h at 37° C. and then for 24-48 h at 42° C. under microaerophilic conditions in Boloton broth media (Oxoid Ltd., UK) and use of an anaerobe jar with an active catalyst and a microaerophilic gas generator pack. Serial 10-fold dilutions were made in Maximum Recovery Diluent (Oxoid Ltd., UK) and the viable cell numbers of *C. jejuni* were determined by surface plating on Columbia Blood agars (Oxoid Ltd., UK)

Monoclonal and polyclonal antibodies: Monoclonal antibody for *Salmonella Typhimurium, Salmonella Enteritidis*, Monoclonal antibody *Campylobacter jejuni* and Polyclonal antibody for *Staphylococcus aureus* as purified liquid were purchased from Biospacific (5980 Horton Street, Ste 360. Emeryville, and CA94608).

Nano-spheres: Cabo blue, tangerine orange and shamrock green beads solutions with polymer description P(S/V-COOH) and surface functional groups (COOH/1) was purchased from (Bangs Laboratories, Inc.), and magnetic beads (TurboBeads Carboxyl) with average size less than 50 nm and maximum size less than 100 nm were purchased from (Turbobeads Llc).

Experimental Procedure

Immobilization of protein on cotton: Activation of the cotton swab (with aldehyde groups): 2.4 g Sodium periodate (NaIO$_4$) was mixed with 100 ml of distilled water and 1 ml of H$_2$SO$_4$ for 10 minutes, then the cotton swab was soaked in the aforementioned solution overnight, next day the cotton swap was washed extensively using distilled water, now the cotton is functionalized with aldehyde groups.

Immobilization of protein (the specific substrate): 40 μl of antibody were mixed well with 1 ml of phosphate buffer for 3 minutes. Then the cotton swab was soaked in the solution and left overnight. Next, it was washed using phosphate buffer (PBS). Then the cotton swab was incubated with 1 ml of bovine serum albumin (BSA) for 30 minutes followed by washing with PBS 3 times. Now the cotton swab is ready to use. It is kept in PBS.

Preparation of the control: Bovine serum albumin (BSA) (1 mg/1 ml) was prepared in PBS and mixed well. Cotton swabs were soaked in the tube containing the prepared solution and left overnight. Next, they were washed well using PBS. Now they are ready for use.

Immobilization of antibody (the specific substrate) on beads: 300 μl of each of the (blue, orange and green) beads or magnetic beads solutions were taken and washed 3 times using 300 μl of water, 1-ethyl-(3-dimethylaminopropyl) carbodimide hydrochloride (EDC) and n-hydroxysuccinimide (NHS) solution was prepared by dissolving 100 mg of (EDC) and 100 mg of (NHS) in 10 ml water followed by well mixing for 2 minutes. Then 300 μl of EDC/NHS solution was added to the beads prepared in a previous step and left for 20 minutes. Consequently the beads were washed three times using PBS. 20 μl of antibody and 300 μl of PBS were added to beads (*Salmonella enteritidis* specific antibody with blue beads, *Salmonella typhimurium* specific antibody with magnetic beads, *Staphylococcus aureus* specific antibody with orange beads and *Campylobacter jejuni* specific antibody with green beads). Then the mixture was left overnight. After the incubation step, the beads were washed with PBS three times. Finally the beads were incubated with 1 ml BSA for 30 minutes. After that the beads were washed using PBS. The beads were stored in PBS.

Assay procedure: One drop of *Salmonella typhimurium, Salmonella enteritidis* or *Staphylococcus aureus, Campylobacter jejuni* solution was spread onto each of the glass slide or stainless steel surfaces and some other drops were spread onto a slide of chicken meat. Subsequently all of the surfaces and the chicken slide were swapped using cotton swab. Then the cotton swabs were washed two times using PBS before soaking in the beads solution for 2 minutes. The blue beads were used to detect *Salmonella enteritidis*, the magnetic beads were used to detect *Salmonella typhimurium*, the orange beads were used to detect *Staphylococcus aureus*. The cotton swabs were then removed from the beads solution 18 and rewashed by PBS for taking a picture, which is illustrated in FIG. 1.

Specificity test: Selectivity of this assay technique for detection of *Salmonella typhimurium* was evaluated by using *Staphylococcus aureus, Escherichia coli* and *Listeria monocytogenes* species separately to contaminate the test surfaces and using cotton swab in which *salmonella* specific antibody was immobilized to swab the contaminated surfaces, also the ability of the method to differentiate between two *salmonellae* types was tested by using swabs with *Salmonella entritidis* specific antibody to swab surfaces which had been contaminated by *Salmonella typhimurium*, the same procedure has been followed in the specificity tests of *Salmonella entritidis, Staphylococcus aureus* and *Campylobacter jejuni*.

As will be understood by a skilled person, the screening procedure is based on the binding affinity between the specific antibodies immobilized on the nano-sphere surfaces and the antigens (*Salmonella typhimurium* or *Salmonella entritidis, Staphylococcus aureus* and *Campylobacter jejuni*) which had been previously collected from the contaminated surfaces using cotton swabs on which antibodies were immobilized. This binding can be inferred through the permanence of the color on the cotton swab after washing by PBS.

Results show a linear relationship between cell number of bacteria and intensity of colors on the cotton swabs which means that the method can be used not only for qualitative analysis but also for quantitative analysis.

Figure 2A:
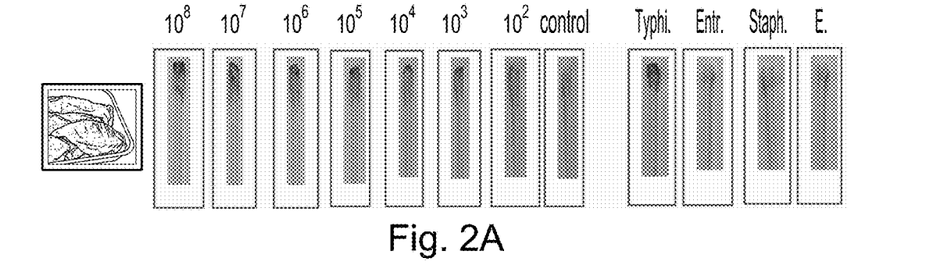
FIGS. 2A, 2B and 2C outlines spiked *Salmonella typhimurium* on three surfaces: 2A. Different concentrations of *Salmonella typhimurium* spiked on chicken. 2B. Different concentrations of *Salmonella typhimurium* spiked on glass slides. 2C. Different concentrations of *Salmonella typhimurium* spiked on stainless steel coupons. For each of 2A, 2B and 2C the four last pictures illustrate specificity.
Figure 2B:
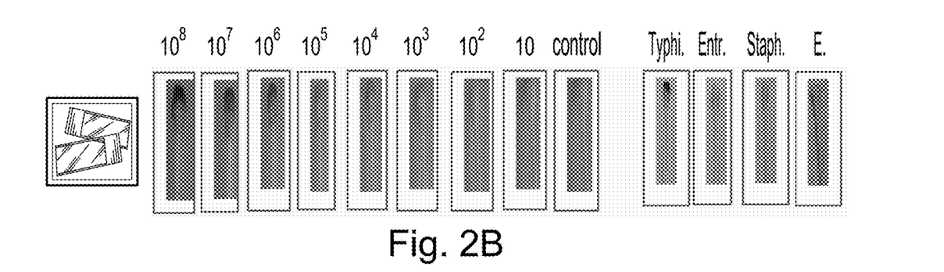
Figure 2C:
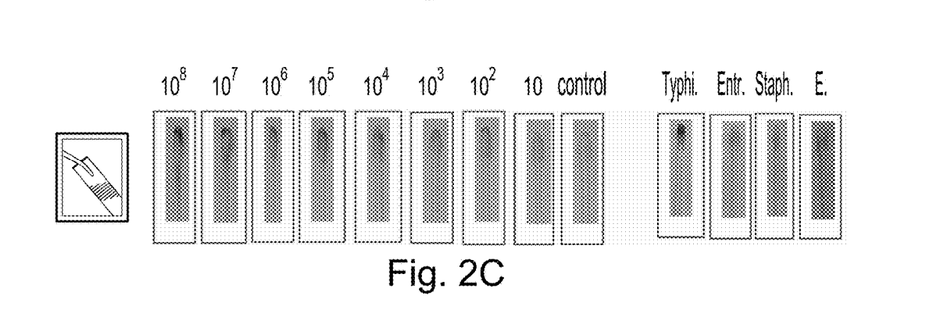

Limits of detection of *Salmonella typhimurium* using magnetic beads were $10^1$, $10^3$ and $10^1$ on spiked chicken meat, glass slide and stainless steel, respectively, as shown in FIGS. 2A, 2B and 2C.

Figure 3A:
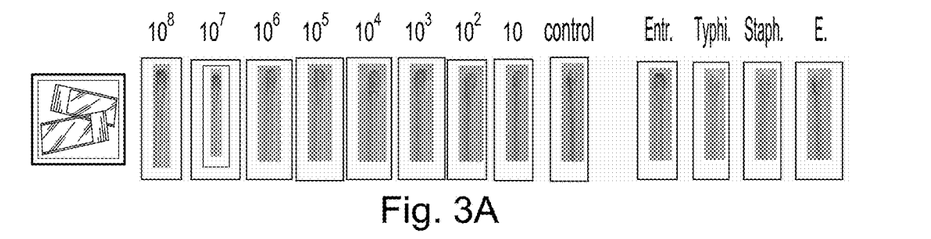
FIGS. 3A, 3B and 3C outlines results obtained with *Salmonella entritidis* on three surfaces: 3A. Different concentrations of *Salmonella entritidis* spiked on glass slides. 3B. Different concentrations of *Salmonella entritidis* spiked on chicken. 3C. Different concentrations of *Salmonella entritidis* spiked on stainless steel. For each of 3A, 3B and 3C the four last pictures illustrate specificity.
Figure 3B:
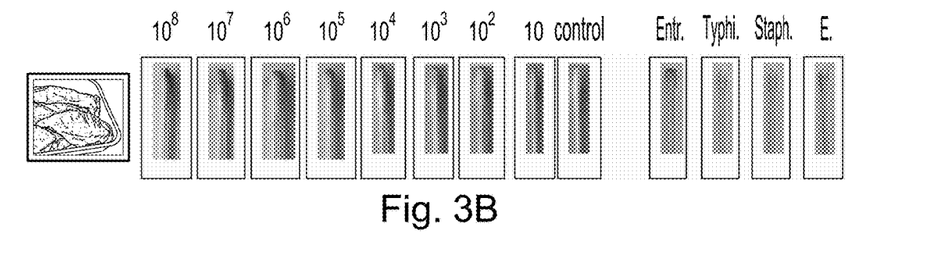
Figure 3C:
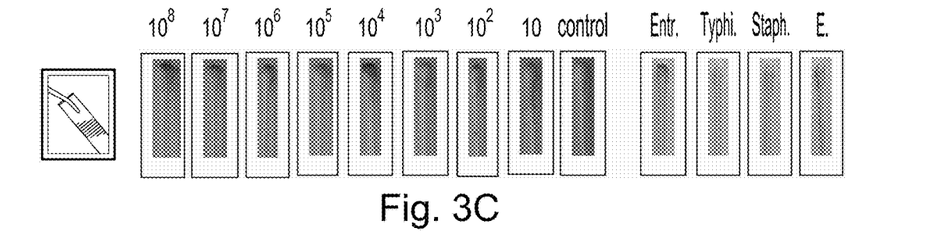

While limits of detection of *Salmonella entritidis* using immobilized specific antibodies on visually dyed nano-spheres (blue beads) were $10^2$, $10^1$, $10^1$ CFU/ml on glass slide, spiked chicken and stainless steel, respectively, as shown in FIGS. 3A, 3B and 3C.

Figure 4A:
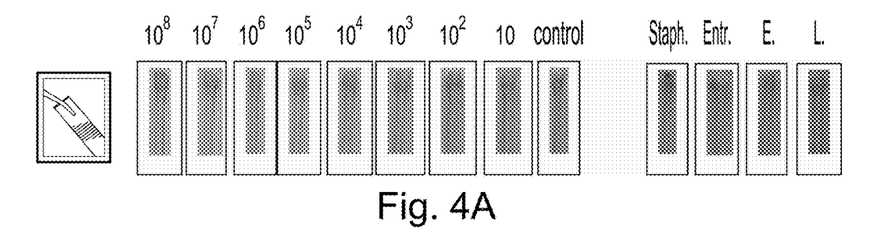
FIGS. 4A, 4B and 4C outlines results obtained with *Staphylococcus aureus* on three surfaces: 4A. Different concentrations of *Staphylococcus aureus* spiked on stainless steel. 4B. Different concentrations of *Staphylococcus aureus* spiked on chicken. 4C. Different concentrations of *Staphylococcus aureus* spiked on glass slides. For each of 4A,4B and 4C the four last pictures illustrate specificity.
Figure 4B:
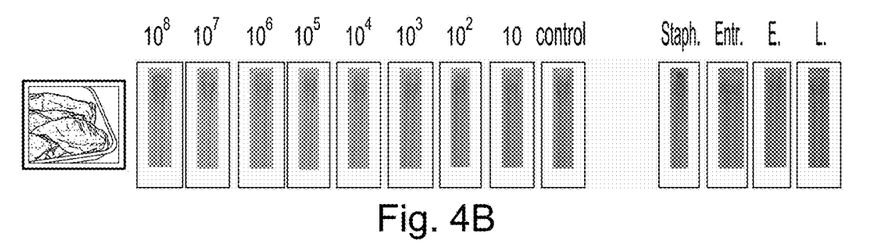
Figure 4C:
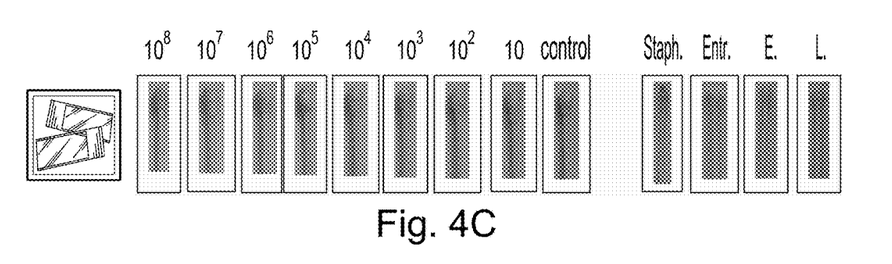

Limits of detection of *Staphylococcus aureus* in the three surfaces using dyed nano-spheres (orange beads) give the lowest values among the three by a limit of detection $10^1$ in all surfaces as shown in FIGS. 4A, 4B and 4C.

Figure 5A:
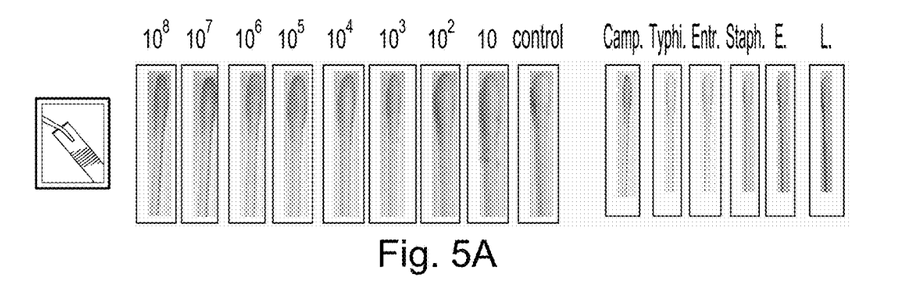
FIG. 5A, 5B and 5C outlines results obtained with *Campilobater jejuni* on three surfaces: 5A. Different concentrations of *Campilobater jejuni* spiked on stainless steel. 5B. Different concentrations of *Campilobater jejuni* spiked on chicken. 5C. Different concentrations of *Campilobater jejuni* spiked on glass slides. For each of 5A, 5B and 5C the four last pictures illustrate specificity.
Figure 5B:
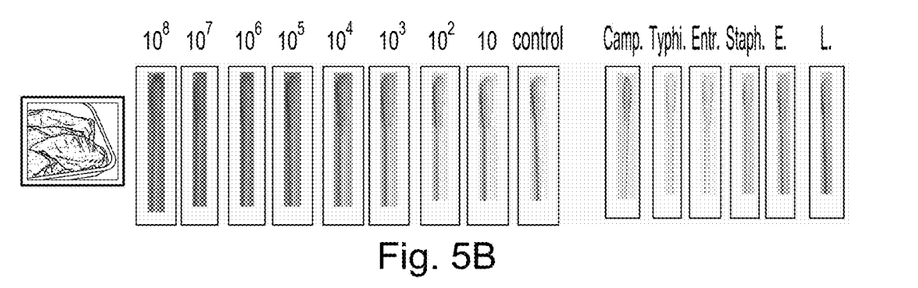
Figure 5C:
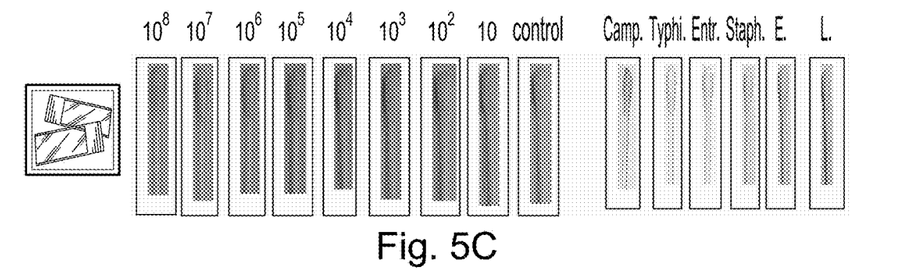

In the case of *Campylobacter jejuni*, the limits of detection were higher than that of the three other strains except that of stainless steel surface as shown in FIGS. 5A, 5B and 5C, results showed limits of detection $10^3$ in both chicken and glass, and $10^1$ in the stainless steel surface.

Specificity tests for detection of the four strains show a good selectivity by which we can easily differentiate not only between different strains but also between the different genera of the same species as in the cases of *Salmonella typhimurium* and *Salmonella entritidis*.

Although the present embodiments have been described with reference to specific example embodiments, it will be evident that various modifications and changes may be made to these embodiments without departing from the broader spirit and scope of the various embodiments.

This disclosure refers to a number of documents, the content of which is herein incorporated by reference in their entirety.

INDUSTRIAL APPLICABILITY

Application of quality assurance systems in food industry, specially, hazard analysis and critical control points (HACCP) system requires new methods and techniques to detect problems which may affect the quality of the end product in the shortest time. Poultry industry is one of such industries. The detection method described in this disclosure meets the requirements of fast detection, feasibility, sensitivity and selectivity of results. Also, the method of this disclosure gives lower detection limits than immunoassay-based techniques. Accordingly, the method of this disclosure may be used in various applications including for example for rapid detection of pathogenic bacteria in a patient sample, poultry processing plants, hospitals, schools or any other environment. The specification and drawings are to be regarded in an illustrative rather than a restrictive sense.

What is claimed is:

1. A method of detecting an analyte in a sample, comprising:
   (a) providing a support of a first color, wherein the support is a tip of a cotton swab, wherein the tip of the cotton swab is shaped in form of a cone and made up of a cotton material, the cotton material is wrapped around a stick to form the cotton swab;
   (b) activating the support prior to step (c) to obtain an activated support having a chemical group on a surface thereof;
   (c) attaching on a surface of the support, a chemical substrate having a binding affinity with the analyte to be detected, to obtain a functionalized support;
   (d) contacting the functionalized support with the sample by swabbing the functionalized support over the sample;
   (e) providing a carrier of a second color different from the first color and capable of masking the first color;
   (f) attaching on a surface of the carrier, the chemical substrate having a binding affinity with the analyte, to obtain a functionalized carrier;
   (g) contacting the sample-contacted, functionalized support obtained at step (d) with the functionalized carrier, such that a visual inspection of the support reveals only the second color; and
   (h) submitting the support obtained at step (f) to a step aimed at removing the carrier from the support,
   wherein persistence of the second color is indicative of the presence of the analyte in the sample, and disappearance of the second color is indicative of the absence of the analyte wherein the carrier consists of magnetic beads and step (h) comprises passing the support over a magnet.

2. The method of claim 1, wherein step (g) comprises soaking the functionalized support obtained at step (d) in an aqueous solution containing the functionalized carrier.

3. The method of claim 1, wherein step (h) further comprises a washing step which is performed with a buffer solution including a phosphate buffer solution.

4. The method of claim 1, wherein the analyte is a bacterium selected from the group consisting of *Salmonella typhimurium*, *Salmonella enteritidis*, *Staphylococcus aureus*, *Campylobacter jejuni*, *Listeria monocytogenes* and *Escherichia coli*.

5. The method of claim 1, wherein the chemical substrate is of biological origin.

6. The method of claim 1, wherein the chemical substrate is a specific recognition receptor having a binding affinity with a specific pathogen, or the chemical substrate is a general recognition receptor having a binding affinity with a group of pathogens.

7. The method of claim 1, wherein the chemical substrate is selected from the group consisting of an antibody, a fragment of an antibody, a peptide, an aptamer, a protein, an engineered protein, a polymeric receptor and a chemical receptor.

8. The method of claim 1, wherein the magnetic beads consist of nano-spheres capable of attaching the chemical substrate on their surface.

9. The method of claim 1, wherein the first color is a white color.

10. The method of claim 1, wherein the second color is selected from the group consisting of black, green, blue, yellow, red, purple and a combination thereof.

11. The method of claim 1, wherein the carrier consists of a set of colored beads of the same color or of different colors.

12. The method of claim 11, wherein the set of colored beads are of the same color.

13. The method of claim 1, wherein the sample is from a patient, a food source, a meat source, a food processing plant, a meat processing plant, a human, an animal, a hospital, a grocery store, or a school.

* * * * *